United States Patent
Gorman et al.

(10) Patent No.: US 6,363,788 B1
(45) Date of Patent: Apr. 2, 2002

(54) NONINVASIVE DETECTION OF CORROSION, MIC, AND FOREIGN OBJECTS IN CONTAINERS, USING GUIDED ULTRASONIC WAVES

(75) Inventors: Michael R. Gorman, Englewood; Steven M. Ziola, Littleton, both of CO (US)

(73) Assignee: Digital Wave Corporation, Englewood, CO (US)

( * ) Notice: Subject to any disclaimer, the term of this patent is extended or adjusted under 35 U.S.C. 154(b) by 0 days.

(21) Appl. No.: 09/613,705

(22) Filed: Jul. 11, 2000

Related U.S. Application Data
(60) Provisional application No. 60/209,796, filed on Jun. 7, 2000.

(51) Int. Cl.[7] .................................. G01N 29/00
(52) U.S. Cl. ........................ 73/597; 73/598; 73/622; 73/624; 73/644
(58) Field of Search .................. 73/570, 597, 599, 73/52, 587, 590, 290, 620, 622, 624, 643, 644, 598, 600

(56) References Cited

U.S. PATENT DOCUMENTS

| | | | | |
|---|---|---|---|---|
| 4,843,884 A | * | 7/1989 | House et al. ................. | 73/622 |
| 4,890,496 A | * | 1/1990 | Biring et al. ................. | 73/597 |
| 5,031,456 A | * | 7/1991 | Askwith et al. .............. | 73/587 |
| 5,295,120 A | * | 3/1994 | McShane ..................... | 367/188 |
| 5,526,689 A | * | 6/1996 | Coulter et al. ................ | 73/592 |
| 5,723,791 A | * | 3/1998 | Koch et al. ................... | 73/597 |
| 5,734,588 A | * | 3/1998 | Rose et al. ................... | 73/644 |
| 5,767,410 A | * | 6/1998 | Lareau et al. ................. | 73/623 |
| 5,922,945 A | * | 7/1999 | Allmaras et al. .............. | 73/52 |
| 5,970,434 A | * | 10/1999 | Brophy et al. ................ | 73/584 |
| 6,105,431 A | * | 8/2000 | Duffill et al. ................. | 73/624 |
| 6,186,004 B1 | * | 2/2001 | Kaduchak et al. ........... | 73/596 |

\* cited by examiner

*Primary Examiner*—Hezron Williams
*Assistant Examiner*—Jacques Saint-Surin
(74) *Attorney, Agent, or Firm*—Jonathan Alan Quine; Quine Intellectual Property Law Group, P.C.

(57) ABSTRACT

Ultrasonic energy in the form of guided waves (plate waves or Lamb waves) is launched into the wall of a container. The guided wave propagates around the circumference of the container from a transmitting transducer to a receiving transducer. Analysis of the received waves determines the presence of corrosion pitting and MIC nodules on the container inner wall, as well as the existence of foreign objects in intimate contact with the container wall. The guided waves are created with wideband transducers excited at certain frequencies that depend on the material and geometry of the part being measured. The guided wave ultrasonic energy is maximized with a shaped tone burst pulse at the specified frequency rather than an electrical spike commonly used to excite transducers in standard ultrasonic search units. The energy and energy ratio of both the direct and wrap fields are measured and related to the container inner wall condition and the presence of any corrosion in the container or obstructions in intimate contact with the container wall.

39 Claims, 2 Drawing Sheets

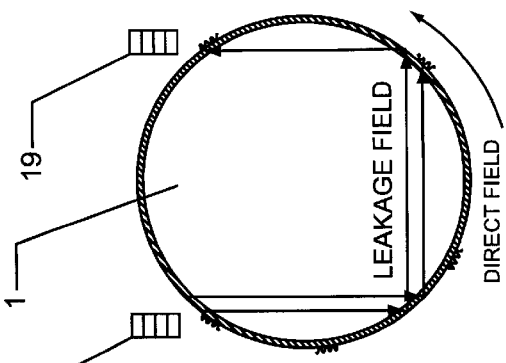
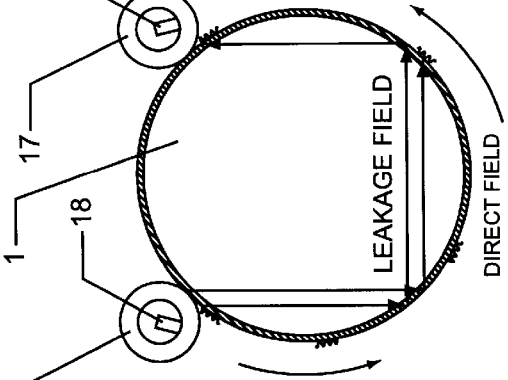
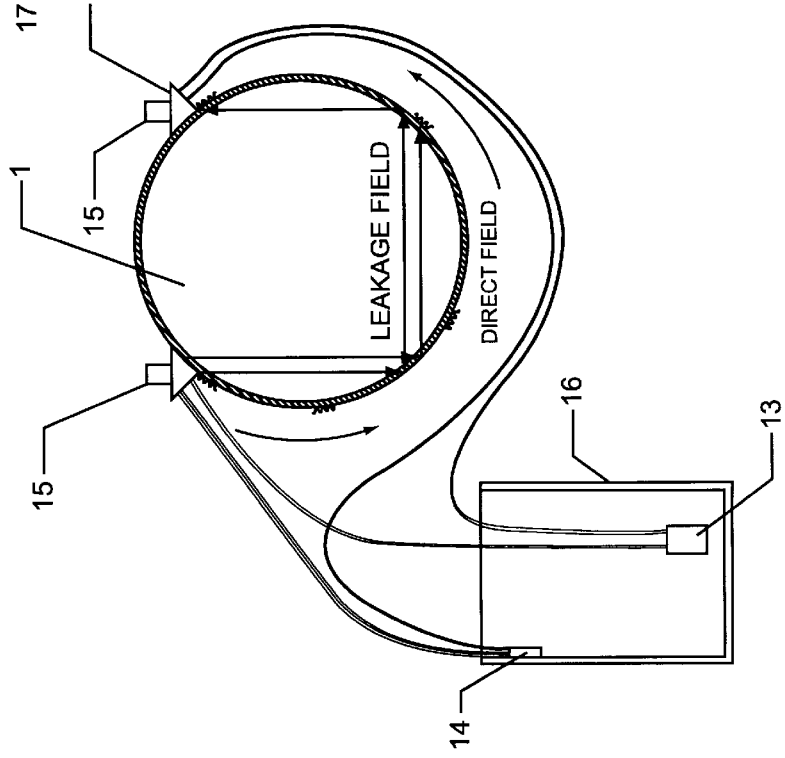

NONINVASIVE DETECTION OF CORROSION, MIC, AND FOREIGN OBJECTS IN CONTAINERS, USING GUIDED ULTRASONIC WAVES

CROSS REFERENCE TO RELATED APPLICATIONS

This application is related to NONINVASIVE DETECTION OF CORROSION, MIC, AND FOREIGN OBJECTS IN PIPES USING GUIDED ULTRASONIC WAVES" by Gorman and Ziola, U.S. Ser. No. 60/209,796, filed Jun. 7, 2000. This application claims priority to this prior application, pursuant to 35 U.S.C. §119(e), as well as any other applicable rule or statute. This application is also related to "NONINVASIVE DETECTION OF CORROSION, MIC, AND FOREIGN OBJECTS IN FLUID-FILLED PIPES USING LEAKY GUIDED ULTRASONIC WAVES" by Gorman et al., U.S. Ser. No. 60/143,366, filed Jul. 12, 1999 and to "NONINVASIVE DETECTION OF CORROSION, MIC, AND FOREIGN OBJECTS IN FLUID-FILLED PIPES USING LEAKY GUIDED ULTRASONIC WAVES" by Gorman et al., U.S. Ser. No. 60/203,661, filed May 12, 2000, and to "NONINVASIVE DETECTION OF CORROSION, MIC, AND FOREIGN OBJECTS IN FLUID-FILLED PIPES USING LEAKY GUIDED ULTRASONIC WAVES" by Gorman et al., Ser. No. 09/613,704 filed Jul. 11, 2000.

FIELD OF INVENTION

This invention relates to noninvasive testing of the internal conditions of containers such as pipes, especially to a novel ultrasonic method for noninvasive testing purposes.

COPYRIGHT NOTICE

Pursuant to 37 C.F.R. 1.71 (e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Detecting inner wall corrosion in containers such as pipes, cylinders, tanks, pressure vessels, etc. has been a longstanding concern in many industries. For example, MIC (microbiologically influenced corrosion) in water systems is of particular concern. Microbes live in water everywhere and are difficult to kill. Corrosion pitting, slimy fluid and rusty nodules are often the products of MIC. Such corrosion and foreign objects cause wall thinning and reduction of flow area that are detrimental to the structural performance of pipes or other containers, and can sometimes lead to disastrous consequences. Chemical, petroleum, water utility, fire and power industries have been battling MIC and other forms of internal container (e.g., pipe) corrosion (e.g., in water and other fluid storage and/or conducting systems) for many years.

Many nondestructive or noninvasive methods have been applied, with varying degrees of success, to locating MIC and assessing its effects. X-ray and gamma ray radiographs provide images that can be used to gauge the presence of MIC, the amount of occlusion and wall thinning. However, drawbacks of these methods include slow inspection speed, high cost and safety/health concern issues.

Ultrasonic thickness gauging is used routinely to measure wall thickness in refinery piping and tanks. Compared to radiography, ultrasound is cheaper and doesn't emit harmful radiation. A single thickness gauge measurement is much faster than radiography, but it only covers a localized area the size of the transducer. Thus, to obtain the thickness information over a large area, the ultrasonic thickness gauge method may not be as fast as radiographic methods. More importantly, a wall thickness reading at a given point depends on good through-thickness echoes so that an accurate time can be measured. Rough corroded internal wall surface and porous MIC nodules make it difficult to get a valid reading. Often the wall thickness reading is greater than nominal. In some cases, no echoes are available because the ultrasonic energy is simply absorbed or scattered. The ultrasonic thickness gauge cannot be used to detect the existence of slimy fluid either.

The present invention provides a new guided wrap wave ultra sound method which is particularly useful in testing dry containers, and which overcomes the limitation of the prior art.

In contrast, the present application relates to a method which uses guided wrap wave ultrasound (GWWU), which is particularly useful in testing dry containers such as pipes, e.g., containers that are not fluid filled.

SUMMARY OF THE INVENTION

A "guided wrap wave ultrasound" (GWWU) method is described for fast and reliable detection of container features such as pitting, loss, thinning, or irregularities of container wall material, container wall corrosion, MIC, etc. The methods herein are also suitable for detecting foreign objects in containers, e.g., objects such as ice or inner wall attachments which are in contact with the inner wall of the container. Inner wall attachments can be deliberate (e.g., structural features of the container) or unintended (e.g., unwanted ice in a pipe or other container).

The methods herein are well-suited to testing containers (e.g., pipes, conduits, tanks, barrels, drums, cylinders, plates and other appropriate structures that will be apparent upon further review of the following) that are not filled with fluids. In particular, containers that are not fluid filled are particularly suitable for testing according to the methods, devices and systems herein (e.g., essentially or putatively empty or dry containers such as dry pipes, empty cylinders, etc.).

In the methods of the invention, a transmitting transducer excites a guided wave in the container wall (the transducer is, e.g., placed circumferentially on the outside of the container). The guided wave travels along the container wall and enters the receiving transducer. The GWWU method measures resulting direct fields and/or wrap waves. Since the direct field and wrap wave interact with the inner and outer surfaces of the pipe wall, the GWWU method is able to reliably detect container features such as corrosion and MIC on the container inner wall (as well as the outer wall), and any foreign objects or structures in intimate contact with the inner or outer walls.

The GWWU measurement can also be used to detect the existence of ice in the container due to frozen condensation water, e.g., if the ice is attached to the container wall, as well being able to detect other materials attached to or contacting the inner container wall.

In addition, a single GWWU measurement covers a significant portion of the circumference of the inner wall. Therefore, as few as two or three GWWU measurement locations can provide essentially 100% inspection coverage of the whole container (e.g., pipe, etc.) circumference. Thus, the inspection speed is faster than any prior method.

The present invention also provides devices, apparatus, integrated systems and kits for practicing the methods of the invention. For example, the invention provides an integrated system and/or device for detecting corrosion and MIC on the inner wall of containers, and foreign objects in contact with the inner wall of the container, using guided wrap wave ultrasound (GWWU).

The system/device includes components for performing the methods herein, such as a transmitting transducer and a receiving transducer configured for placement at circumferential positions of a pipe or other container, a guided wave generator which produces a shaped tone burst pulse at a specified frequency and means for measuring the direct field, thereby providing an indication of existence of corrosion and MIC on the pipe inner wall, and foreign objects in contact with the pipe inner wall. Typically, direct field and/or wrap waves are the received signals resulting from guided wave propagation along the pipe.

The guided wave can be excited at a selected frequency and angle to maximize the direct field for selected container ODs and materials. Other suitable wave characteristics can also be selected or modulated in the methods and systems herein; e.g., the amplitude of a given phase point on the tone bursts can be modulated or selected.

The device, apparatus, kit or system can include a computer or computer readable medium (or multiple associated computers or computer media) having an instruction set for controlling the system e.g., including an instruction set for controlling the system e.g., for controlling the transmitting transducer the guided wave generator, or the like. The computer or computer readable medium can include other relevant instruction sets, e.g., for measuring the direct field and the leakage field, reporting the results of the measurement to a user, recording and analyzing the direct field energy and wrap wave energy, and the like. Kits can include any of the apparatus or integrated systems elements plus containers for storing the apparatus or system elements, instructions in using the apparatus or integrated systems elements, packaging, etc.

A presently preferred method/system is to use an arbitrary function generator (which, e.g., generates a pulse at a user-defined frequency) in combination with a wideband transducer, so that a range of frequencies can be excited and received. This approach typically uses computer software to control and shape the pulse and frequency along with wideband amplifiers and filters. The system device includes the geometrical configurations and various media that can be used to couple the transducers to the container, tank or structure.

Further objects and advantages of the invention will become apparent from a consideration of the drawings and description.

BRIEF DESCRIPTION OF THE FIGURES

FIG. 2 panels A–C provide a schematic of three different ways of implementing the GWWU transducer coupling system 3 and 4 in FIG. 1.

DETAILED DISCUSSION OF THE INVENTION

List of Reference Numerals

Figure 1:
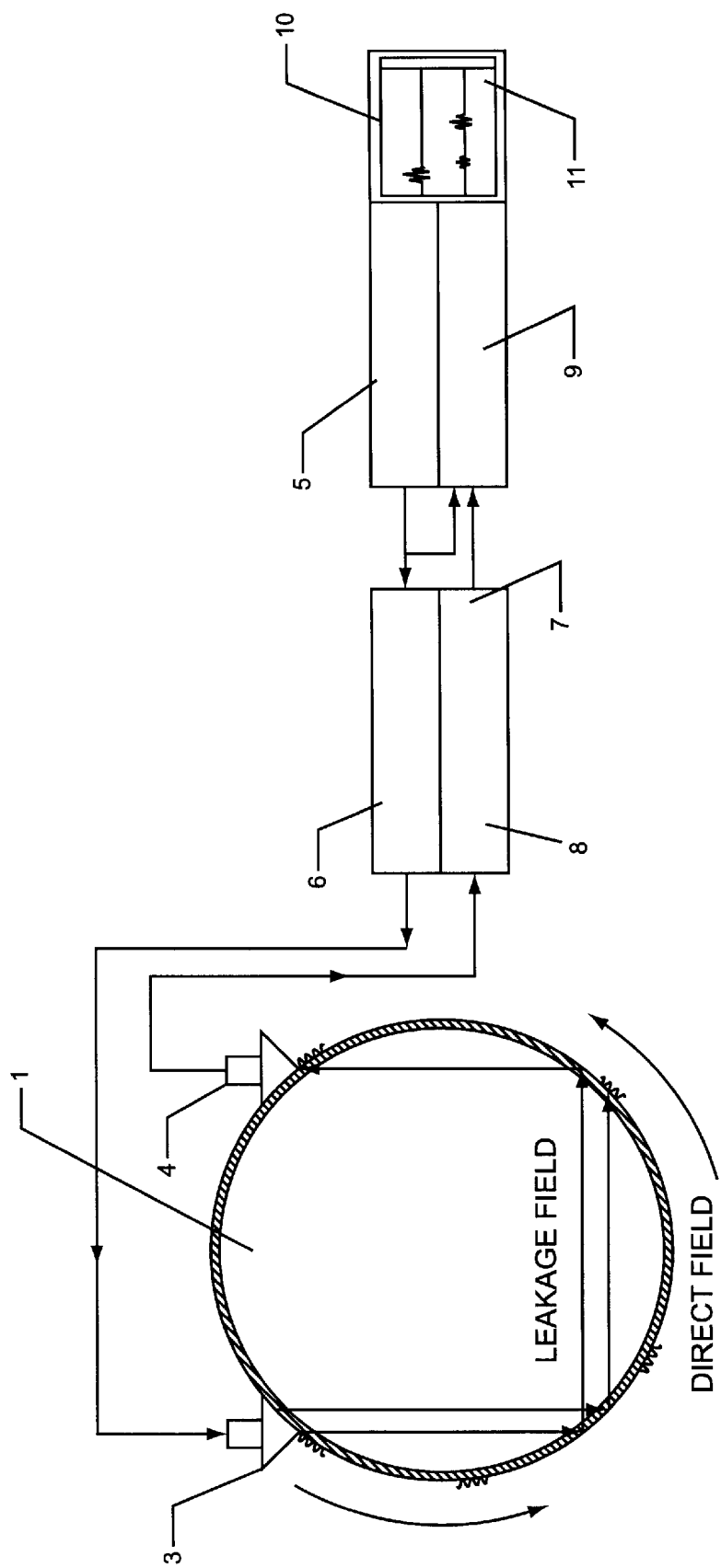
FIG. 1 is a schematic of the GWWU measurement system.
Figure 1:
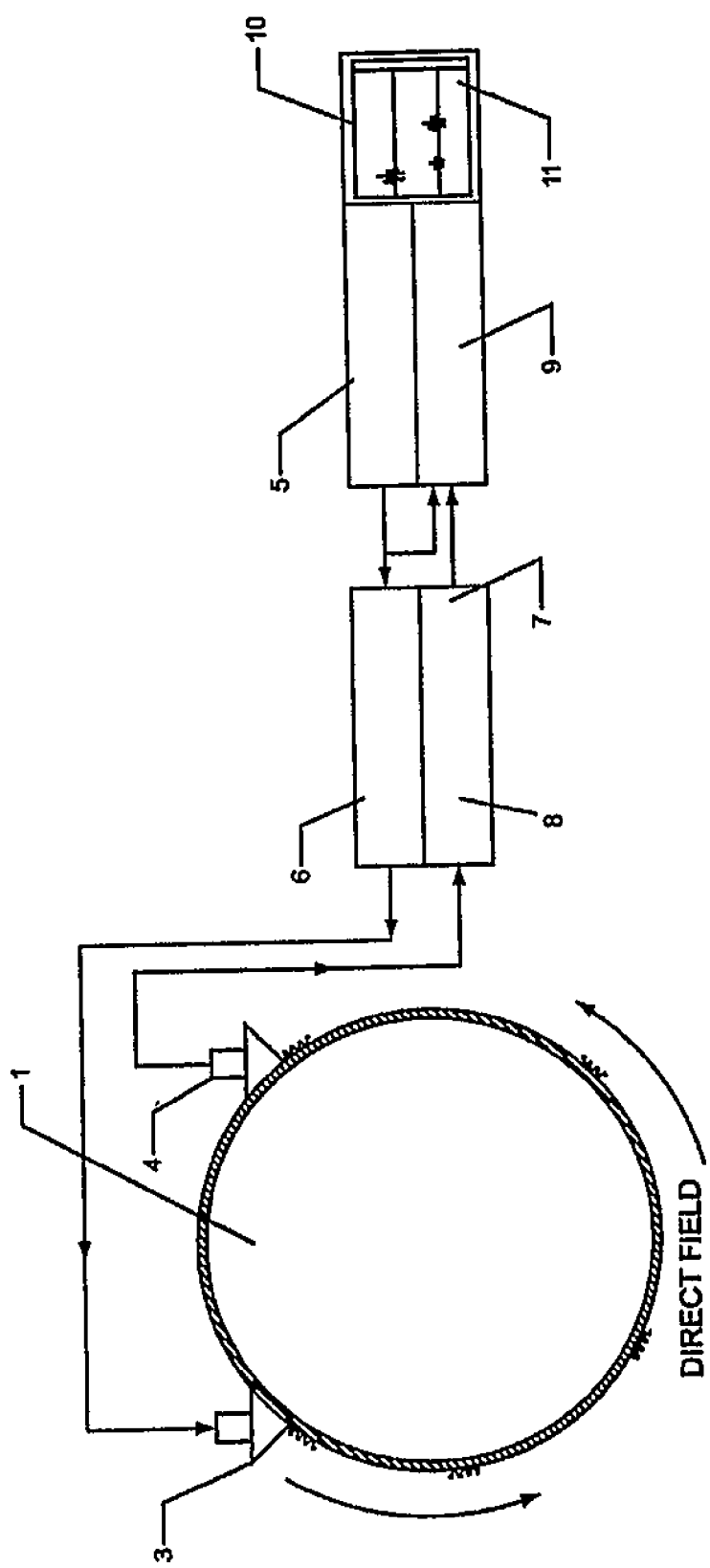

The reference numerals below correspond to elements of the figures.

1—dry pipe or other container
3—transmitting transducer coupling system
4—receiving transducer coupling system
5—arbitrary function generator
6—RF amplifier
7—RF receiver—gain circuitry
8—RF receiver—filter circuitry
9—2—channel A/D converter
10—computer
11—energy field detection/display module, comprising GWWU elements
12—wedge shoe
13—water pump
14—vacuum pump
15—contact transducer
16—water bucket
17—rubber wheel
18—immersion transducer
19—Air-coupled transducer Patent applications regarding the use of ultrasonic testing using guided waves have been filed by the current inventors. In the applications, leaky guided wave ultrasonics are used to detect internal corrosion and obstructions, e.g., in pipes. In those patent applications, the containers are generally filled with fluid for the detection of obstructions and corrosion. A transmitting transducer excites the guided wave, and part of its energy leaks into the fluid. The leaky wave travels through the fluid, reflects off the container inner wall and enters a receiving transducer. Since the leakage field interacts directly with the fluid and inner container wall, the leaky guided wave ultrasonic (LGWU) method is able to reliably detect the corrosion and MIC on the pipe inner wall, and any foreign objects inside the fluid. See, e.g., "NONINVASIVE DETECTION OF CORROSION, MIC, AND FOREIGN OBJECTS IN FLUID-FILLED PIPES USING LEAKY GUIDED ULTRASONIC WAVES" by Gorman et al., U.S. Ser. No. 60/143,366, filed Jul. 12, 1999 and "NONINVASIVE DETECTION OF CORROSION, MIC, AND FOREIGN OBJECTS IN FLUID-FILLED PIPES USING LEAKY GUIDED ULTRASONIC WAVES" by Gorman et al., U.S. Ser. No. 60/203,661, filed May 12, 2000.

Introduction: Guided Wave Ultrasonic Testing

Guided ultrasonic waves can be used to overcome the speed limitation of an ultrasonic thickness gauge. A typical ultrasonic thickness gauge involves a standard "flashlight" beam pulse-echo ultrasonic testing (UT) at a point, and only one transducer is used as both the transmitter and receiver.

In contrast, guided wave ultrasound (GWU) travels in the areal direction along the axis or circumference of the pipe wall rather than in the thickness direction. Typically two transducers placed on the wall surface several inches apart are used in GWU; one acts as the transmitter and the other as the receiver.

The physics of these different approaches is quite different, as might be expected. Standard UT involves bulk or free waves at wavelengths much smaller than the wall thickness, and the waves can be treated as small tight packets travelling inside the wall in the thickness direction. GWU wavelengths are on the order of the wall thickness or greater, and the wave packets occupy the whole wall thickness and travel in the areal direction along the wall. Thus, the GWU can propagate great distances along the wall area only slightly diminished, like light in optical fibers. Bulk waves propagate without dispersion while GWU waves are dispersive. In GWU, different frequencies in the wave packet propagate at different velocities and pulses will change shape as they travel along. Finally, instead of the two wave modes as in standard UT, there are many modes in GWU.

The physics of guided waves was described by Lamb in 1917, and Mindlin in the 1950s & 1960s, but little technology in industrial container testing resulted until the early 1990s. As advanced microprocessors made the difficult GWU computations possible, there was an increased interest in the industrial application of GWU.

Currently, there are at least two GWU applications in container testing commonly mentioned in the literature. The first is container thickness measurement where a received pulse travels directly from a transmitter to a receiver along the container wall, a known distance, at a known velocity. Since the spacing between the transmitter and receiver is much greater than the transducer size, the GWU thickness measurement is much faster than the ultrasonic thickness gauge measurement. Note that the GWU wall thickness is an integrated wall thickness over the line between the transmitter and receiver. The other GWU application is for crack detection, e.g., where a single transducer is used as both the transmitter and receiver to listen to the GWU echoes from cracks in the wall.

In both cases, the GWU measurements rely on the GWU waves whose energy is distributed through the whole wall thickness. Thus, the GWU measurement is sensitive to corrosion conditions existing on both the inner and outer wall. In the present invention, guided wrap wave ultrasound (GWWU) is used to detect wall thickness and is also used to detect the MIC nodules or slimy fluid inside the pipe or other container as the waves are affected by the existence of such features.

The GWWU method is sensitive to the existence of corrosion on the pipe outer wall surface. Paint and dust have little effect on the measurement due to the large impedance and stiffness mismatch to the pipe material.

DESCRIPTION OF PREFERRED EMBODIMENTS

It will be understood that the methods and apparatus herein are used for examining the inner or outer walls of any type of container. As used herein, the term "container" is intended broadly to apply to any structure that can be said to encompass a given volume, or even to define a portion of a given volume. Such structures include, without limitation, pipes and other conduits, whether partly or fully open or partly or fully closed, tanks, cylinders, plates, pressure vessels, etc. In general, when specifically referring to any of these (e.g., pipes) herein, it will be appreciated that similar methods, apparatus, devices systems, etc., can be applied to any similar structural form.

FIG. 1 shows a basic schematic of a guided wrap wave ultrasound (GWWU) system of the invention. One of skill will recognize a variety of features that may be substituted to achieve essentially similar results; however, for clarity, the following discussion focuses on this basic system.

The system, which interfaces with dry pipe or other container 1 comprises transmitting transducer coupling system 3, receiving transducer coupling system 4, RF amplifier 6, RF receiver gain 7 and filter 8 circuitry, computer 10 with plug-in arbitrary function generator 5, 2-channel A/D converter 9, and analysis/display software. An output of 5 is connected to an input of RF amplifier 6. This output can optionally be input into channel 1 of A/D converter 9 for reference. RF amplifier 6 output is connected to transmitting transducer 3. The receiving transducer is connected to an input of RE receiver gain 7 and filter 8 circuitry. The output of the RF receiver is connected to the channel 2 input of the A/D converter 9. Energy field detection/display module 11 controls, e.g., the signal generation, acquisition and display functions. The energy field detection module optionally comprises an analog to digital converter, which converter converts direct or leakage field energy into digital format data. Arbitrary function generator 5 can, e.g., generate a pulse at a user defined frequency.

Software and/or hardware present in the energy field detection/display module 11 (this module can include software, firmware, hardware, or a combination thereof for data analysis and display, including analog and/or digital display formats) controls function generator 5 to generate a tone burst pulse with selectable frequency, amplitude, shape, cycles in the pulse and pulsing rate. The shaped tone burst pulse out of function generator 5 is sent to the channel 1 input of A/D converter 9 and displayed on the computer screen, e.g., as depicted as the upper trace. The same pulse is also sent simultaneously to the input of RF amplifier 6. After amplification, the pulse is then sent to wideband transmitting transducer 3 to excite the guided wave in the container wall. The excited guided wave propagates along the circumference in the metal wall. The received signal is then amplified and filtered by gain 7 and filter 8 circuitry of the RF receiver.

The conditioned signal is then sent to channel 2 input of A/D converter 9, and displayed on the computer screen (depicted as the lower trace). Note that display/software for energy field detection/display module 11 can also define data acquisition parameters such as the A/D rate, total digitized time window, etc. Alternately, these parameters can be controlled separately, e.g., using a different module in computer 10, or a second computer.

The user can create a calibration wave using the software for each container wall thickness, diameter, and material. This wave can be displayed, allowing the user to visually compare the calibration wave with the wave from the container being inspected.

The user can create a calibration wave using the software for each container wall thickness, diameter, and material. This wave can be displayed, allowing the user to visually compare the calibration wave with the wave from the container being inspected. This is a helpful component of the system, providing for accuracy and reliability when in use by trained personnel. It should be noted that this form of display is novel to the present system.

For pipes or other containers of different OD and wall thicknesses, a specific group of frequencies and transducer coupling systems has been selected to maximize the excitation of the direct field from the well-known theory of guided waves. The frequency range for GWWU wave generation is between about 20 kHz to about 1.5 MHz, with sensor angles between about 30° and about 70° from the normal to the pipe or other container surface. The excitation of the direct energy is determined by the frequency of the ultrasound, property of the coupling medium and the wall material and thickness. If there exists corrosion on the wall inner surface, or if there is an obstruction in intimate contact with the container wall, the direct energy is reduced due to absorption and scattering. This phenomenon can be used to detect corrosion and MIC nodules on the inner wall, ice due to frozen condensation water, denser fluid such as slimy fluid, and the existence of foreign objects in intimate contact with the container wall. Data analysis/display software for energy field detection/display module 11 analyzes the direct field energy, wrap wave energy (multiple trips of the wave around the circumference) and then classifies the condition of the pipe or other container (of course, separate software modules can be substituted in place of a single software module).

Generally, the software controls the transmission and reception of the ultrasonic pulse, performs specific analyses to evaluate and categorize the container condition, and displays both raw signals and analysis results in a user friendly format. To measure properly, the type of container is input into a database, which can be added to as necessary or desired. This database includes, e.g., the material, schedule and diameter of the container, etc.

A feature of the software optionally provides calibration. For example, by selecting a "CAL" button on the screen, a standard waveform for a new container of that material, schedule and diameter is displayed just above that of the container being tested. This provides the operator with a useful visual comparison to supplement the analysis algorithms. This becomes particularly helpful when the container schedule changes unexpectedly, as it often does, e.g., in older systems that have undergone repairs.

The following provides a basic flowchart/outline of the operations performed by an exemplar software module:
1. Select pipe or other container parameters (schedule and diameter).
2. Select measurement, e.g., thickness or obstruction.
3. Select calibration waveform (this is optional)
4. Acquire data: pulse shape and frequency are downloaded from an internal database; the pulse is sent out of the pulser board in the computer. The pulse is amplified and excites the transmitting transducer. The pulse is detected by the receiving transducer, fed to receiver electronics, and then fed into an analog to digital converter and stored in digital electronic format in the computer.
5. Analyze data: received waveform(s) is/are compared with calibration signal(s), with both regular and wrap waves being tested.
6. Raw data is displayed as received signal(s) and analysis result(s).
7. Stored calibration pulse waveform for good container (s) are displayed.

The direct field energy and wrap energy are not greatly affected by the existence of paint or dust so the GWWU method can be used on pipes or other containers without much surface preparation. Corrosion on the outer surface, however, will affect the measurement but, normally, containers are corroded on the inside rather than on the outside. Furthermore, the main issue in testing is often internal pipe or other container conditions, as external conditions can often be assessed by simple visual inspection.

For each measurement, the direct field covers a significant portion of the pipe or other container circumference. Therefore, only two or three measurements in the circumferential direction are needed to completely inspect the pipe or other container inner wall and the fluid inside.

Water-coupled wideband transducers, dry-coupled wideband transducers, and an air-coupled wideband transducer are all examples of appropriate transducers for the present invention. FIG. 2 shows three different ways of implementing GWWU transducer coupling system 3 and 4 in FIG. 1. For the water-coupled system shown in FIG. 2-A, contact transducer 15 is mounted on a wedge shoe 12 with ultrasonic gel in between. The bottom surface of shoe 12 is machined to match the contour of the pipe or other container outer surface. In addition, water holes are drilled into the bottom surface. Water tubes are used to connect the water holes to water pump 13 in water bucket 16, and to vacuum pump 14 attached to the side water bucket 16 above the water line. Water pump 13 pumps water to the shoe bottom to provide coupling between the wedge shoe and container outer surface. The excess water is sucked up by vacuum pump 14 and flows back into water bucket 16.

For the dry-coupled system shown in FIG. 2-B, immersion transducer 18 is placed inside fluid-filled rubber wheel 17 (it will be appreciated that materials such as polymers, plastics or the like can be substituted for the rubber on the rubber wheel). The wheel rotates while the transducer sits at a fixed angle towards the container. The fluid couples the ultrasound from the sensor to the rubber wheel. The rubber on the outside surface of the wheel deforms to the outside diameter of the container, and is coupled to the container using a small amount of ultrasonic couplant. Air-coupled systems like that in FIG. 2-C can also be used. Air-coupled transducer 19, such as an electromagnetic transducer (EMAT), are placed at a fixed angle above the container.

The objective of the coupling system is to couple the ultrasound out of the transmitting sensor and into the container to become guided waves propagating away from the system along the container wall. At the same time, it also couples the ultrasound traveling towards the receiving coupling system into the receiving transducer.

Accordingly, the guided wrap wave ultrasound (GWWU) system provides a fast and reliable device to detect corrosion and MIC on the container inner wall, and foreign objects inside the container in intimate contact with the inner container wall. While the above description contains many specific examples, these should not be construed as limitations on the scope of the invention, but rather as an exemplification of embodiments thereof. Many other variations are possible and will be apparent to one of skill upon review of this disclosure. For example, one can perform MIC detection by placing the transducers axially rather than circumferentially. This would increase the inspection area, reducing inspection times. Another example is to apply the same GWWU system to inspect containers of non-circular shapes, such as cubes and cones (i.e., conic and cubic shapes, or any other regular or irregular shapes).

Other uses of the GWWU method include detection of objects attached to the wall. For example, the trays inside a distillation column, vanes and partitions inside a tank, hat stiffeners in an aircraft wing, reinforcements and other attachments for walls of a container. The advantage of using the GWWU method in those applications is that one can determine whether something is attached to the wall anywhere on the circumference, without having to inspect the entire circumference point by point. This approach is much faster, more reliable and more versatile than the standard UT point-by-point method.

Variations of transducer coupling systems 3 and 4, other than those specifically described above, can also be used. These include, but are not limited to, dry couplant, laser, electrostatic transducers, air scanners, rollers, touch and release fixtures, back reflected energy with a single transducer etc. Similarly, plug-in function generator 5 can comprise or be replaced by a stand-alone analog function generator, and computer 10 with plug-in A/D converter 9 can also be substituted, e.g., by a digital or analog oscilloscope. The system optionally includes an analog energy detector and digital or analog display.

The foregoing description of embodiments of the invention has been presented for purposes of illustration and description. The description is not intended to be exhaustive or to limit the invention to the precise form disclosed, and many modifications and variations are possible in light of the above teaching. Such modifications and variations which may be apparent to a person skilled in the art are within the scope of this invention. All patent documents and publications cited above are incorporated by reference in their entirety for all purposes to the same extent as if each item were so individually denoted.

What is claimed is:

1. A method for detecting container features, or materials attached to the container, by guided wrap wave ultrasound (GWWU), the method comprising:
   (a.) placing a transmitting transducer and a receiving transducer at circumferential positions of a container;
   (b.) generating guided waves using a shaped tone burst pulse at a specified frequency; and,
   (c.) measuring a direct field and/or wrap waves, thereby providing an indication of existence of corrosion and obstructions on the container inner wall, and foreign objects inside the container in contact with the container wall.

2. The method of claim 1, wherein the container comprises one or more of: a dry pipe, a dry conduit, a dry tank, a dry barrel, a dry drum, a dry cylinder, and a dry plate.

3. The method of claim 1, wherein the container comprises one or more of: a circular region, a conic region, and a cubic region.

4. The method of claim 1, wherein the container features, or materials attached to the container wall comprise one or more of: corrosion on the inner wall of the container, MIC on the inner wall of the container, a foreign object attached to the inner wall and ice on the inner wall of the container.

5. The method of claim 4, wherein said corrosion comprises pitting or loss of wall material on the container inner wall.

6. The method of claim 4, wherein said MIC comprises microbiology-induced corrosion.

7. The method of claim 4, wherein said foreign objects is any slimy fluid or inner wall attachment.

8. The method of claim 1, wherein said transducer comprises a water-coupled wideband transducer, a dry-coupled wideband transducer, or an air-coupled wideband transducer.

9. The method of claim 1, wherein said guided waves are waves excited at a selected frequency and angle to maximize the direct field for selected container ODs and materials.

10. The method of claim 1, wherein said measuring includes recording and analyzing the direct field energy and wrap wave energy.

11. The method of claim 10, wherein the amplitude of a given phase point on the tone burst is selected or modulated.

12. The method of claim 1, wherein said direct field and/or wrap waves are the received signals due to guided wave propagation along the container.

13. An integrated system for detecting container features, or materials attached to the container, by guided wrap wave ultrasound (GWWU), the system comprising:
   (a.) a transmitting transducer and a receiving transducer placed at circumferential positions of a container;
   (b.) a guided wave generator which produces a shaped tone burst pulse at a specified frequency; and,
   (c.) an energy field detection module for measuring both a direct field and a wrap field, which measurement provides an indication of container features or materials inside the container.

14. The integrated system of claim 13, wherein the container comprises one or more of: a dry pipe, a dry tank, a dry barrel, a dry drum, a dry cylinder, and a dry plate.

15. The integrated system of claim 13, wherein the container comprises one or more of: a circular region, a conic region, and a cubic region.

16. The integrated system of claim 13, wherein the container features, or materials attached to the container wall comprise one or more of: corrosion on the inner wall of the container, MIC on the inner wall of the container, a foreign object attached to the inner wall and ice on the inner wall of the container.

17. The integrated system of claim 13, comprising a computer or computer readable medium comprising an instruction set for controlling the transmitting transducer, or the guided wave generator.

18. The integrated system of claim 13, comprising a computer or computer readable medium comprising an instruction set for measuring the direct and wrap fields.

19. The integrated system of claim 13, comprising a computer or computer readable medium comprising an instruction set for measuring the direct and wrap fields and an additional instruction set for reporting the results of the measurement to a user.

20. The integrated system of claim 19, said instruction set comprising instructions for recording and analyzing the direct and wrap field energy.

21. The integrated system of claim 13, wherein said transducer comprises a water-coupled wideband transducer, a dry-coupled wideband transducer, or an air-coupled wideband transducer.

22. The integrated system of claim 13, wherein the energy field detection module comprises an analog to digital converter, which converter converts direct or leakage field energy into digital format data.

23. The integrated system of claim 22, the detection module comprising a digital display, which digital display provides a user-viewable display of information in the digital format data.

24. The integrated system of claim 12, wherein the energy field detection module comprises an analog energy detector and an analog display.

25. The integrated system of claim 13, the detection module comprising means for measuring the direct and leakage field.

26. A device for detecting container features, or materials attached to the container, by guided wrap wave ultrasound (GWWU), the device comprising:
   (a.) a transmitting transducer and a receiving transducer configured to be placed at circumferential positions of a container;
   (b.) a guided wave generator which produces a shaped tone burst pulse at a specified frequency; and,
   (d.) means for measuring a direct and wrap fields, thereby providing an indication of existence of corrosion and MIC on the container inner wall, and foreign objects inside the container in contact with the container wall.

27. The device of claim 26, wherein the container comprises one or more of: a dry pipe, a dry tank, a dry barrel, a dry drum, a dry cylinder, and a dry plate.

28. The device of claim 26, wherein the container comprises one or more of: a circular region, a conic region, and a cubic region.

29. The device of claim 26, wherein the container features, or materials attached to the containers comprise one or more of: corrosion on the inner wall of the container, MIC on the inner wall of the container, ice on the inner wall of the container, or one or more foreign object or material attached to an inner wall of the container.

30. The device of claim 26, further comprising a computer or computer readable medium comprising an instruction set for measuring the direct and wrap fields and an additional instruction set for reporting the results of the measurement to a user.

31. The integrated system of claim 30, said instruction set comprising instructions for recording and analyzing the direct and wrap field energy.

32. The method of claim 31, wherein the amplitude of a given phase point on the tone burst is selected or modulated.

33. The device of claim 26, wherein said transducer comprises a water-coupled wideband transducer, a dry-coupled wideband transducer, or an air-coupled wideband transducer.

34. The device of claim 26, further comprising a computer with a plug-in arbitrary function generator and analysis/display software.

35. The device of claim 34 further comprising a 2-channel A/D converter.

36. The device of claim 34, wherein the arbitrary function generator generates a pulse at a user-defined frequency.

37. The device of claim 34, wherein the arbitrary function generator generates a pulse at a user-defined frequency and wherein an output of the arbitrary function generator is connected to a first channel input of the A/D converter.

38. The device of claim 26, further comprising a transmitting transducer coupling system, a receiving transducer coupling system, a RF amplifier, a RF receiver gain and filter circuitry, a computer with a plug-in arbitrary function generator, a 2-channel A/D converter, and an analysis/display software.

39. The device of claim 38, wherein the arbitrary function generator generates a pulse of user-defined frequency and wherein:

the output of the arbitrary function generator is connected to a first channel input of the A/D converter and to an input of the RF amplifier;

the RF amplifier output is connected to the transmitting transducer;

the receiving transducer is connected to an input of the RF receiver gain and filter circuitry;

the output of the RF receiver is connected to a second channel input of the A/D converter; and, the data analysis/display software controls signal generation, acquisition and display functions.

* * * * *

UNITED STATES PATENT AND TRADEMARK OFFICE
CERTIFICATE OF CORRECTION

PATENT NO. : 6,363,788 B1
DATED : April 2, 2002
INVENTOR(S) : Michael R. Gorman et al.

It is certified that error appears in the above-identified patent and that said Letters Patent is hereby corrected as shown below:

<u>Title page,</u>
Item [60], Related U.S. Application Data, should read as follows:
-- Provisional application No. 60/209,796, filed June 5, 2000. --

Signed and Sealed this

Twenty-ninth Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,363,788 B1  Page 1 of 4
APPLICATION NO. : 09/613705
DATED : April 2, 2002
INVENTOR(S) : Michael R. Gorman et al.

It is certified that error appears in the above-identified patent and that said Letters Patent is hereby corrected as shown below:

Title page, should be deleted to be replaced with the attached title page.

Drawing sheets, consisting of Figs. 1–2 should be deleted to be replaced with the attached sheets.

Signed and Sealed this

Twenty-seventh Day of November, 2007

JON W. DUDAS
*Director of the United States Patent and Trademark Office*

United States Patent
Gorman et al.

(10) Patent No.: US 6,363,788 B1
(45) Date of Patent: Apr. 2, 2002

(54) NONINVASIVE DETECTION OF CORROSION, MIC, AND FOREIGN OBJECTS IN CONTAINERS, USING GUIDED ULTRASONIC WAVES

(75) Inventors: Michael R. Gorman, Englewood; Steven M. Ziola, Littleton, both of CO (US)

(73) Assignee: Digital Wave Corporation, Englewood, CO (US)

(*) Notice: Subject to any disclaimer, the term of this patent is extended or adjusted under 35 U.S.C. 154(b) by 0 days.

(21) Appl. No.: 09/613,705

(22) Filed: Jul. 11, 2000

Related U.S. Application Data

(60) Provisional application No. 60/209,796, filed on Jun. 7, 2000.

(51) Int. Cl.⁷ .............................................. G01N 29/00
(52) U.S. Cl. ............................ 73/597; 73/598; 73/622; 73/624; 73/644
(58) Field of Search ............................. 73/570, 597, 599, 73/52, 587, 590, 590, 620, 622, 624, 643, 644, 598, 600

(56) References Cited

U.S. PATENT DOCUMENTS

| | | | |
|---|---|---|---|
| 4,843,884 A | * | 7/1989 | House et al. ................ 73/622 |
| 4,890,496 A | * | 1/1990 | Binog et al. ................ 73/597 |
| 5,031,456 A | * | 7/1991 | Askwith et al. ............. 73/587 |
| 5,295,120 A | * | 3/1994 | McShane .................... 367/188 |
| 5,526,689 A | * | 6/1996 | Coulter et al. .............. 73/592 |
| 5,723,791 A | * | 3/1998 | Koch et al. ................. 73/597 |
| 5,734,588 A | * | 3/1998 | Rose et al. ................. 73/644 |
| 5,767,410 A | * | 6/1998 | Lareau et al. .............. 73/623 |
| 5,922,945 A | * | 7/1999 | Allmaras et al. ............ 73/52 |
| 5,970,434 A | * | 10/1999 | Brophy et al. .............. 73/584 |
| 6,105,431 A | * | 8/2000 | Duffill et al. ............... 73/624 |
| 6,186,004 B1 | * | 2/2001 | Kaduchak et al. .......... 73/598 |

\* cited by examiner

*Primary Examiner*—Hezron Williams
*Assistant Examiner*—Jacques Saint-Surin
(74) *Attorney, Agent, or Firm*—Jonathan Alan Quine; Quine Intellectual Property Law Group, P.C.

(57) ABSTRACT

Ultrasonic energy in the form of guided waves (plate waves or Lamb waves) is launched into the wall of a container. The guided wave propagates around the circumference of the container from a transmitting transducer to a receiving transducer. Analysis of the received waves determines the presence of corrosion pitting and MIC nodules on the container inner wall, as well as the existence of foreign objects in intimate contact with the container wall. The guided waves are created with wideband transducers excited at certain frequencies that depend on the material and geometry of the part being measured. The guided wave ultrasonic energy is maximized with a shaped tone burst pulse at the specified frequency rather than an electrical spike commonly used to excite transducers in standard ultrasonic search units. The energy and energy ratio of both the direct and wrap fields are measured and related to the container inner wall condition and the presence of any corrosion in the container or obstructions in intimate contact with the container wall.

39 Claims, 2 Drawing Sheets

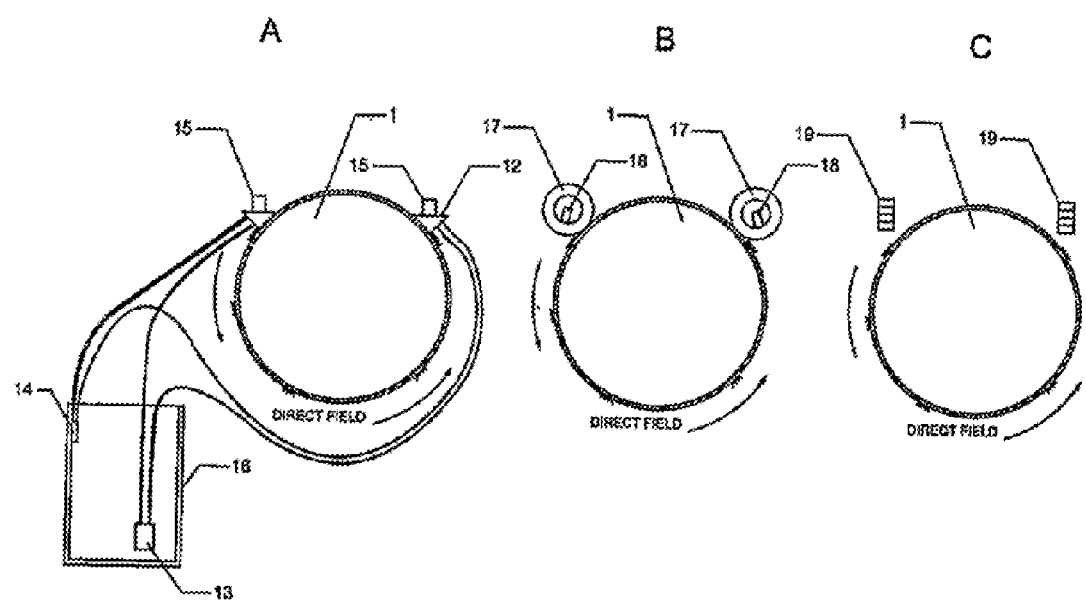

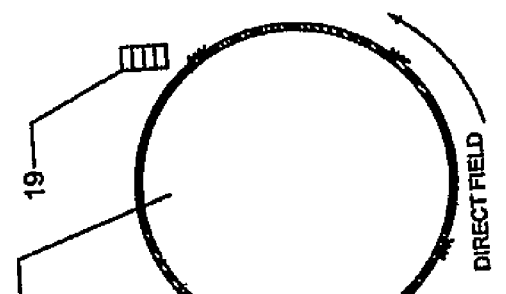
Fig. 2C
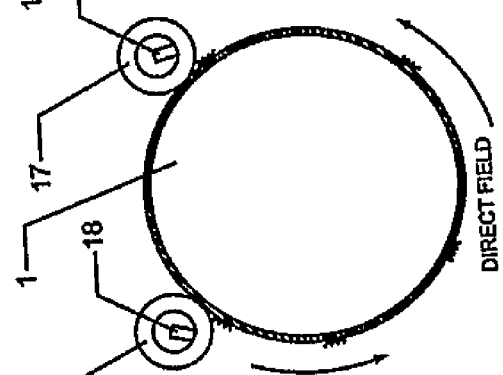
Fig. 2B
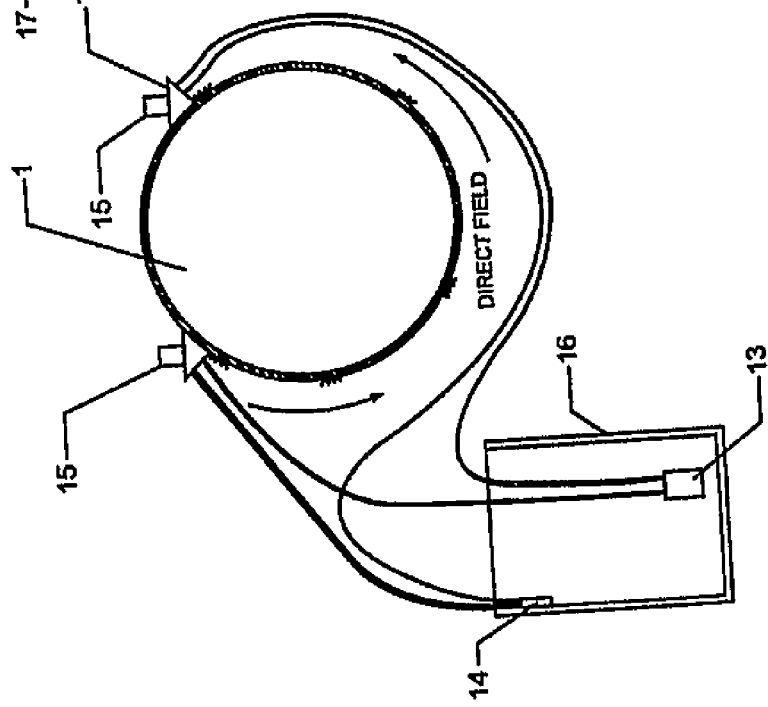
Fig. 2A
Fig. 2